US005453291A

United States Patent [19]

Sasahara et al.

[11] Patent Number: 5,453,291

[45] Date of Patent: Sep. 26, 1995

[54] FRP MEMBER AND METHOD OF DETECTING INTERNAL DAMAGE THEREIN

[75] Inventors: Jun Sasahara, Kawagoe; Hajime Goto, Asaka, both of Japan

[73] Assignee: Honda Giken Kogyo Kabushiki Kaisha, Tokyo, Japan

[21] Appl. No.: 391,823

[22] Filed: Feb. 21, 1995

Related U.S. Application Data

[63] Continuation of Ser. No. 65,893, May 25, 1993, abandoned.

[51] Int. Cl.[6] .............................. B05D 3/14; G01N 27/82

[52] U.S. Cl. .............................. 427/8; 324/240; 324/238; 324/237

[58] Field of Search ................................ 427/8; 324/238, 324/216, 237, 240, 226

[56] References Cited

U.S. PATENT DOCUMENTS

| | | | |
|---|---|---|---|
| 4,803,428 | 2/1989 | Crostack | 427/8 |
| 4,944,185 | 7/1990 | Clark, Jr. et al. | 73/579 |

FOREIGN PATENT DOCUMENTS

| | | |
|---|---|---|
| 60-114741 | 6/1985 | Japan . |
| 2-271227 | 11/1990 | Japan . |
| 5-142130 | 6/1993 | Japan . |

*Primary Examiner*—Shrive Beck
*Assistant Examiner*—Katherine A. Bareford

[57] ABSTRACT

The detection of an internal damage in an FRP member constituted by reinforcing fibers, a matrix resin and magnetic members having a magneto-mechanical property is conducted by disposing the magnetic members in the FRP member, and measuring a change in the magnetic properties of the magnetic members by a non-destructive inspection method.

7 Claims, 5 Drawing Sheets

FRP MEMBER AND METHOD OF DETECTING INTERNAL DAMAGE THEREIN

This application is a continuation, of application Ser. No. 08/065,893 filed on May 25, 1993, now abandoned.

BACKGROUND OF THE INVENTION

1. Field Of The Invention

The present invention relates to a member of a fiber-reinforced plastic (hereinafter referred to as "FRP") whose internal damage is easily detected by a non-destructive inspection method, and a method of detecting the internal damage of such an FRP member.

2. Description Of The Prior Art

Since FRPs are excellent in mechanical strength with light weight and can easily be molded or formed into desired shapes, they are used for wide applications in various fields. Despite such excellent characteristics, the FRPs suffer from problems such as micro-cracking, the separation of reinforcing fibers from matrix plastics, etc., which may be caused by impact from outside or fatigue after the lapse of a long period of time. Such defects would lead to the failure of the FRPs.

It is, therefore, important to know a limit until which the FRPs can be used safely. For this purpose, various methods of detecting defects in the FRPs have been proposed so far.

For example, the detection of the extent of internal damage in the FRPs using a light transmission method, an X-ray method, an ultrasonic method or an acoustic emission (AE) method has been developed. However, the light transmission method, the X-ray method and the ultrasonic method are suitable only for detecting relatively large defects, and the AE method requires some troublesome operations such as the application of a load to the FRP member, though it can detect relatively small defects. Further, the AE method gives unsatisfactory precision in the detection of the defects.

As an alternative method, Japanese Patent Laid-Open No. 60-114741 discloses a method of detecting internal damage of FRP members, in which long, conductive carbon fibers are embedded in the FRP member, and electric current is supplied to the long, conductive carbon fibers to measure the electric conductivity of the carbon fibers, by a level of which electric conductivity the extent of internal damage of FRP members can be predicted. This method is based on the principle that if there is an internal damage in the FRP member, some of the carbon fibers would be cut in the damaged portion, resulting in no or reduced electric conductivity of the carbon fibers.

However, since this method requires troublesome and difficult steps of attaching long carbon fibers to surfaces of the reinforcing fiber cloths, this method is not suitable for the mass production of the FRP members. Also, since the long carbon fibers are used, this method is not suitable for FRP members with complicated shapes. Further, this method may accelerate the deterioration of the FRP members because electric current is applied to the conductive carbon fibers contained in the FRP members.

Therefore, a simple detection method of internal damage in FRP members in a non-destructive manner has been desired.

OBJECT AND SUMMARY OF THE INVENTION

Accordingly, an object of the present invention is to provide an FRP member whose internal damage can easily be detected by a non-destructive inspection method even though it has a complicated shape.

Another object of the present invention is to provide a non-destructive inspection method capable of detecting internal damage without difficulty even for an FRP member having a complicated shape.

As a result of intense research in view of the above objects, the inventors have found that if the FRP member contains a member made of a magnetic material having such a magneto-mechanical property that its magnetic properties are changeable greatly when an external stress is applied to the FRP member, the internal damage of the FRP member will be detected without difficulty by sensing a change in the magnetic properties of the magnetic member in the FRP member. The present invention has been completed based on this finding.

Thus, the FRP member according to the present invention comprises reinforcing fibers, a matrix resin and magnetic members having a magneto-mechanical property, wherein a change in the magnetic properties of the magnetic members can be measured to detect an internal damage in the FRP member.

The method of detecting an internal damage of an FRP member according to the present invention comprises the steps of producing the FRP member from reinforcing fibers, a matrix resin and magnetic members having a magneto-mechanical property, measuring a change in the magnetic properties of the magnetic members disposed in the FRP member, thereby detecting an internal damage in the FRP member. Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
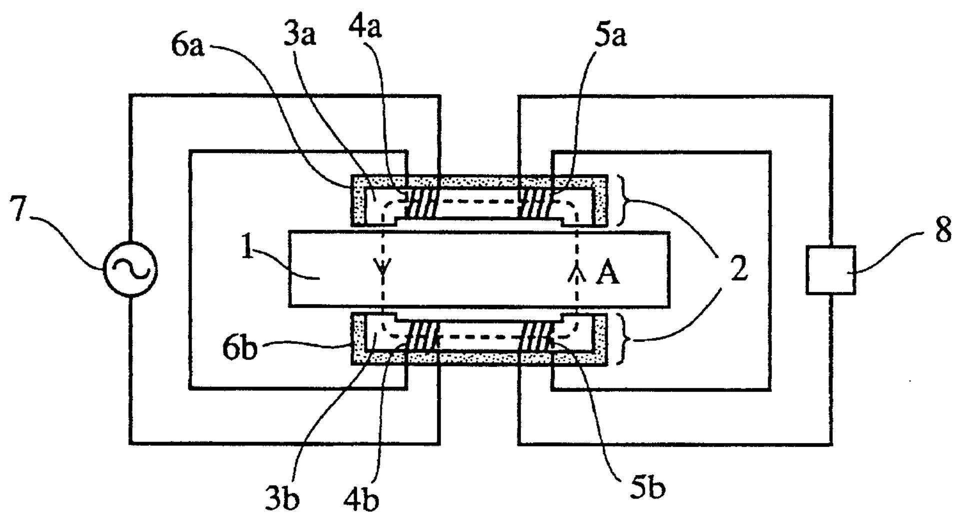
FIG. 1 is a schematic view showing a method of detecting the magnetic properties of the magnetic members in the FRP member according to the present invention.

The present invention will be explained below in detail referring to the drawings attached hereto.

When a matrix resin is cured in the FRP member, reinforcing fibers generally receive tensile or compressive stress at the level of several kg/mm$^2$ from their surrounding matrix resin being cured. Accordingly, if there is an internal damage in the FRP member, such tensile or compressive stress would generate micro-cracks which propagate in the FRP member, and would cause the separation of reinforcing fibers from the matrix resin. Once the micro-cracking and/or the exfoliation takes place, the tensile or compressive stress applied to the reinforcing fibers will gradually be released. If such internal damage as the micro-cracks and the separation of reinforcing fibers from the matrix resin is developed, the FRP member would finally be destroyed.

Therefore, in order to detect the internal damage in the FRP member, it is necessary to measure how much internal stress applied to the reinforcing fibers has been released. It has been found that if a magnetic member having such a magneto-mechanical property that its magnetic properties are greatly changeable with the stress applied thereto is disposed in or on the FRP member to detect the internal damage of the FRP member, and if the change of the magnetic properties is measured, it would be possible to determine a certain level of the change in the magnetic properties above which the FRP member is likely to be destroyed.

The magnetic members usable in the present invention may be made of extremely magnetostrictive materials such as Fe-based amorphous alloys, Fe-rare earth metal alloys, etc. The preferable amorphous alloy is an Fe—Si—B based alloy. More specifically, an amorphous alloy having a composition of 65–67 atomic % of Fe, 8–9 atomic % of Si, 11–13 atomic % of B, 10–12 atomic % of Co and 1–3 atomic % of Cr is preferable. The amorphous alloy having the above-mentioned composition has an excellent magneto-mechanical property as well as an improved corrosion resistance. The improved corrosion resistance is desirable to enhance the service life of the FRP member because the FRP member is generally prone to absorb water.

The magnetic members may be in the form of long fibers (wires), short fibers, ribbons, flakes or powders. Among these shapes, the long fibers (wires) are preferable because they give a high sensitivity in the detection of the internal damage.

When a wire made of the magnetic material is employed, its diameter is preferably 10–200 μm, more preferably 100–150 μm. The production of wires having diameters of less than 10 μm frown the magnetic materials such as Fe-based amorphous alloys is quite difficult. On the other hand, if the diameters of the wires of the magnetic materials are larger than 200 μm, the wire-shaped magnetic materials would not be sufficiently amorphous.

The volume fraction (hereinafter referred to as "v/f") of the magnetic members in the FRP member is preferably 0.1–50%, more preferably 1–10%. If the v/f of the magnetic members is lower than 0.1%, the detection of the change in magneto-mechanical property of the magnetic members would be difficult. On the other hand, if the v/f exceeds 50%, the molding of the FRP member becomes difficult, resulting in the FRP member having a poor specific strength (ratio of strength to density).

Explanation will be made in further detail below, taking the amorphous wire as an example of the magnetic members having a magneto-mechanical property.

The amorphous wires or their woven fabrics such as net-like cloths and reinforcing fiber cloths may be separately produced and incorporated into the FRP member. However, to achieve uniform distribution of the amorphous wires in the FRP member, it is preferable that the amorphous wires are combined with the reinforcing fibers to form blended yarns or blended yarn fabrics, which are then impregnated with the matrix resin to form the desired FRP member. The blended yarn fabrics may be constituted by the blended yarns of the reinforcing fibers and the amorphous wires, but they may be produced by weaving the reinforcing fibers as wefts and the amorphous wires as warps. Also, after forming the FRP member, the amorphous wires may be integrally attached to the FRP member by using the same matrix resin as in the FRP member.

The amorphous wires (including blended yarns and blended yarn fabrics containing the amorphous wires) may be disposed uniformly in the FRP member, or they may be disposed predominantly in a particular portion of the FRP member such as a surface portion in order to enhance the sensitivity in the detection of the magnetic properties. The portion of the FRP member in which the amorphous wires are concentrated may differ depending on the methods of detecting the magnetic properties which will be explained below in detail.

The orientation of the amorphous wires may be preferably in parallel to the direction in which the largest external stress is applied to the FRP member because this orientation is most advantageous in terms of mechanical strength.

The matrix resin of the FRP member may be epoxy resins, unsaturated polyester resins, phenol resins, polyamides, polyether ether ketone, etc. However, other thermosetting or thermoplastic resins used in the conventional FRPs may also be used in the present invention.

The reinforcing fibers usable in the present invention may be glass fibers, carbon fibers, aromatic polyamide fibers, etc. However, the present invention is not restricted to the above fibers and other fibers commonly used as reinforcing fibers in the conventional FRPs may also be used.

The v/f (volume fraction) of the reinforcing fibers in the FRP member is preferably 20–70%, more preferably 55–65%.

The FRP members may be produced by the following method. The blended yarns consisting of the reinforcing fibers and the amorphous wires in a certain proportion are prepared, and the blended yarns are then woven to form fabrics such as net-like cloths. The blended yarn fabrics are impregnated with a matrix resin such as epoxy resins, etc. and then cured by heating or irradiation to form the FRP member. Incidentally, the amorphous wires may be directly disposed in the FRP member without being formed into the blended yarn fabrics and impregnated with a matrix resin.

The measurement of the magneto-mechanical property of the magnetic members disposed in the FRP member can be performed by a magnetic sensor. Any type of magnetic sensors may be employed in the present invention, as long as they have enough sensitivity in the detection of a change in the magneto-mechanical property to determine the extent of the internal damage.

One example of the magnetic sensors usable in the present invention comprises, as schematically shown in FIG. 1, two sensing coils 2, 2 placed on both sides of the FRP member 1 with or without contact with surfaces of the FRP member 1, thereby forming a closed magnetic circuit for measuring the magnetic properties.

As is shown in FIG. 1, first and second U-shaped ferrite cores 3*a*, 3*b* are fixed to inner surfaces of cover members 6*a*, 6*b*, respectively. The first exciting coil 4*a* and the first detecting coil 5*a* are wound around the first ferrite core 3*a* at separate positions. In the same manner, the second exciting coil 4*b* and the second detecting coil 5*b* are wound around the second ferrite core 3*b*. The first and second exciting coils 4*a*, 4*b* are connected to a high-frequency power source 7, and the first and second detecting coils 5*a*, 5*b* are connected to a detector 8.

When the power source 7 supplies a high-frequency current to the first and second exciting coils 4*a*, 4*b*, a closed magnetic circuit having magnetic flux passing through the FRP member 1 as shown by the arrow A in FIG. 1 is generated. An electromotive force induced by this magnetic flux can be sensed by the first and second detecting coils 5*a*, 5*b* and detected as a mutual inductance (simply called "inductance") by the detector 8. Alternatively, the output signal of the magnetic sensor may be detected as a wave distortion factor of alternating current (simply called "distortion factor").

Since the above inductance changes with the stress applied to the amorphous wires (namely the change in magnetic properties of the amorphous wires) disposed in the FRP member 1, the level of the stress can be determined by measuring the inductance.

With respect to the detection sensitivity, the magnetic sensor having a closed magnetic circuit as shown in FIG. 1 is more preferable than pick-up type magnetic sensors described below.

Figure 2:
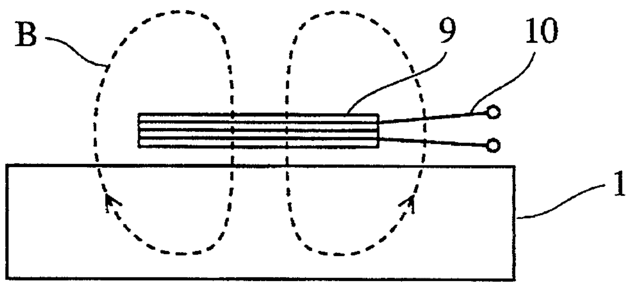
FIG. 2 is a schematic view showing another method of detecting the magnetic properties of the magnetic members in the FRP member according to the present invention.

An alternative magnetic sensor usable in the present invention is a so-called pick-up type magnetic sensor as shown in FIG. 2. This pick-up type magnetic sensor comprises a sensing coil 9 consisting of a flat exciting coil and a flat detecting coil (both not specified in FIG. 2) and lead wires 10. The sensing coil 9 is placed in contact with or slightly apart from the surface of the FRP member 1. When an high-frequency current is supplied to the exciting coil, magnetic circuits shown by the dotted lines B are generated. Since the magnetic circuits pass through the FRP member 1, the internal damage of the FRP member 1 can be detected in the same principle as in the above closed magnetic circuit shown in FIG. 1.

With this pick-up type magnetic sensor, the detection of the internal damage can be easily conducted in the FRP members having complicated shapes.

Figure 3:
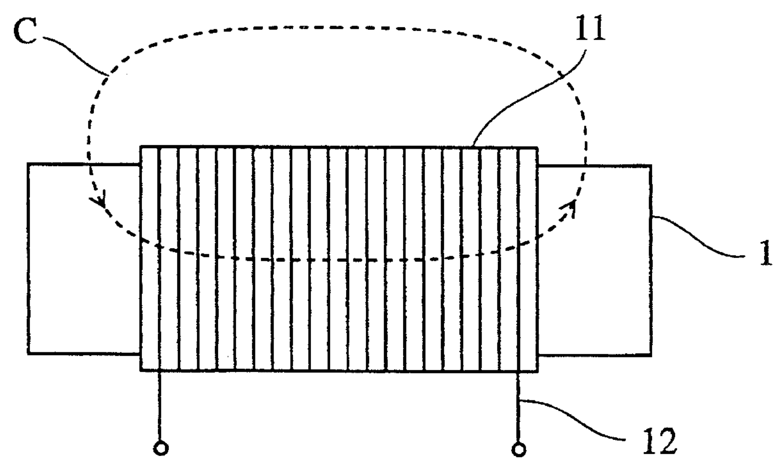
FIG. 3 is a schematic view showing a further method of detecting the magnetic properties of the magnetic members in the FRP member according to the present invention.

A further example of the magnetic sensors is shown in FIG. 3, which comprises a sensing coil 11 consisting of an exciting coil and a detecting coil (both not specified in FIG. 3) and surrounding the FRP member 1, and lead wires 12. In this magnetic sensor, the sensing coil 11 may be disposed with or without contact with the surface of the FRP member 1.

When a high-frequency current is supplied to the sensing coil 11 in the magnetic sensor in FIG. 3, a magnetic circuit shown by the dotted line C is generated, which passes through the FRP member 1. The inductance is measured in the same manner as in the above examples to detect the internal damage in the FRP member 1.

The internal stress applied to the amorphous wires changes with the extent of the internal damage in the FRP member 1, and the magnetic properties of the amorphous wires in turn change with the internal stress applied to the amorphous wires. The change of the magnetic properties of the amorphous wires can be detected as a change in the inductance of the magnetic sensor as shown, for instance, in FIG. 6 which is a graph showing that the inductance of the magnetic sensor changes with a periodically changing tensile stress applied to the FRP member. Incidentally, some degree of tensile stress may remain in the FRP member and then be released gradually depending on the types of the reinforcing fibers, the orientation of the amorphous wires and positions to which stress is applied.

Figure 6:
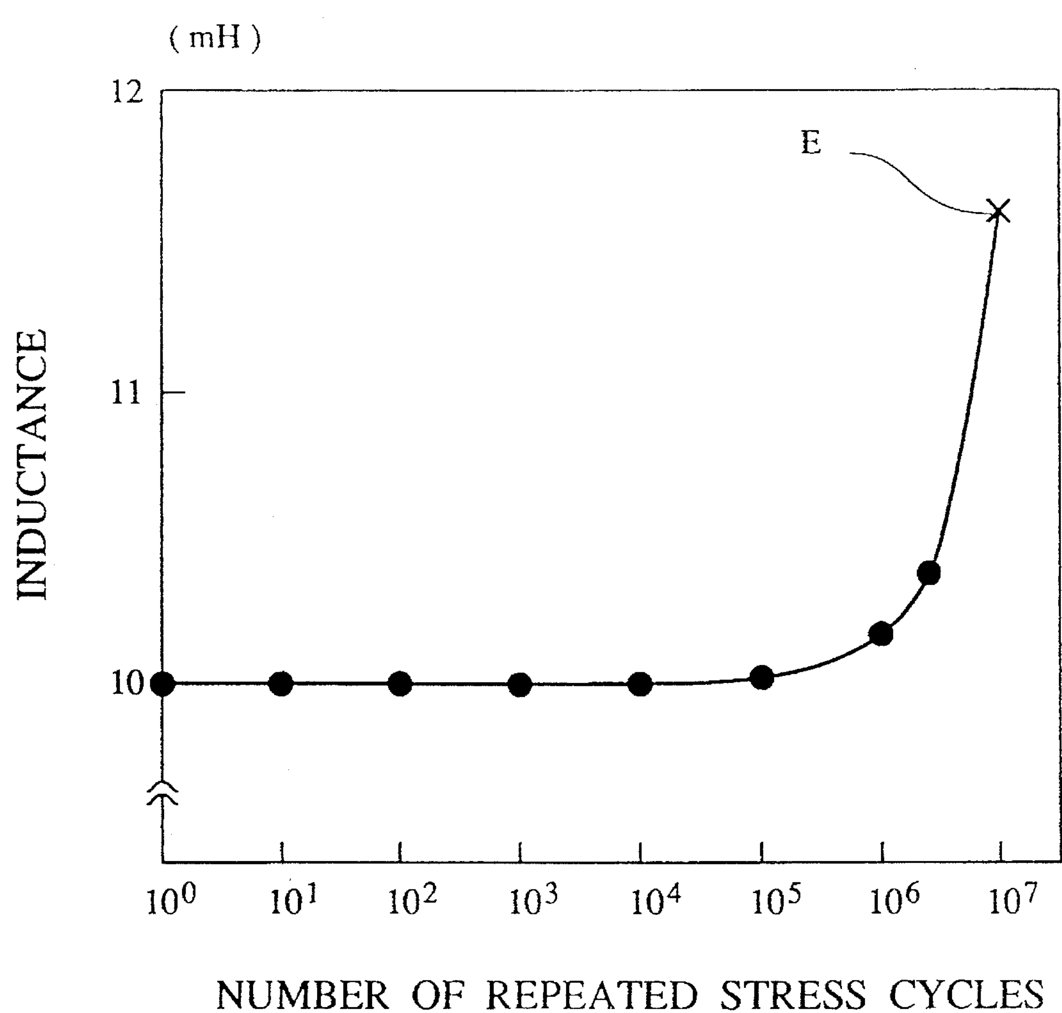
FIG. 6 is a graph showing the relation between the number of stress cycles and the inductance in Example 1.

For instance, as is clear from FIG. 6, the change in inductance is quite small in an early stage in which there is little damage due to the fatigue, but the inductance changes drastically slightly before the fatigue failure takes place at the point E. By this drastic change in the inductance, the limit of use can be determined. In one preferred example, it is determined that when the inductance changes (increases) by 10% of the initial value, the FRP member has reached the limit of use. However, it should be noted this level of deciding the limit of use may be changed properly depending on the FRP members.

The present invention will be explained in further detail by the following Examples without intention of restricting the scope of the present invention.

EXAMPLE 1

Glass fibers having an average diameter of 8 μm and wires made of an amorphous Fe-base alloy having a composition consisting essentially of 66.5 atomic % of Fe, 8.5 atomic % of Si, 12 atomic % of B, 11 atomic % of Co, and 2 atomic % of Cr and having an average diameter of 30 μm were combined together to make blended yarns in a volume fraction (glass fibers/amorphous wires) of 14/1, and the resulting blended yarns were woven to form a blended yarn cloth having a size of 25 mm×250 mm.

The blended yarn cloth was impregnated with an epoxy resin. A plurality of the blended yarn cloths were laminated with reinforcing fabrics of glass fibers in a die, and the epoxy resin was introduced into the die in such an amount that a volume ratio of the fibers (glass fibers+ blended yarns) to the epoxy resin was 6-4. After forming an epoxy resin-impregnated laminate into a desired shape, it was heat-cured at 120° C. for two hours to provide an FRP test piece having a size of 25 mm×250 mm×2 mm. Incidentally, the amorphous wires were located in a surface portion of the FRP test piece, and the orientation of the amorphous wires was in parallel to the direction in which an external stress was applied to the FRP test piece in the following test. In the FRP test piece, a v/f of the glass fibers was 56%, a v/f of the amorphous wires was 4%, and a v/f of the epoxy resin was 40%.

Figure 4:
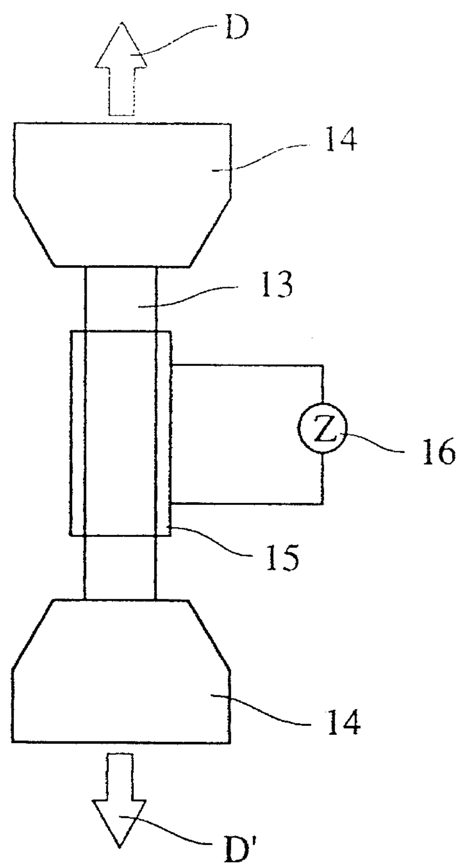
FIG. 4 is a schematic view showing a method of detecting the magnetic properties of the magnetic members in an FRP test piece to which a periodically changing tensile stress was applied in Example 1.
Figure 5:
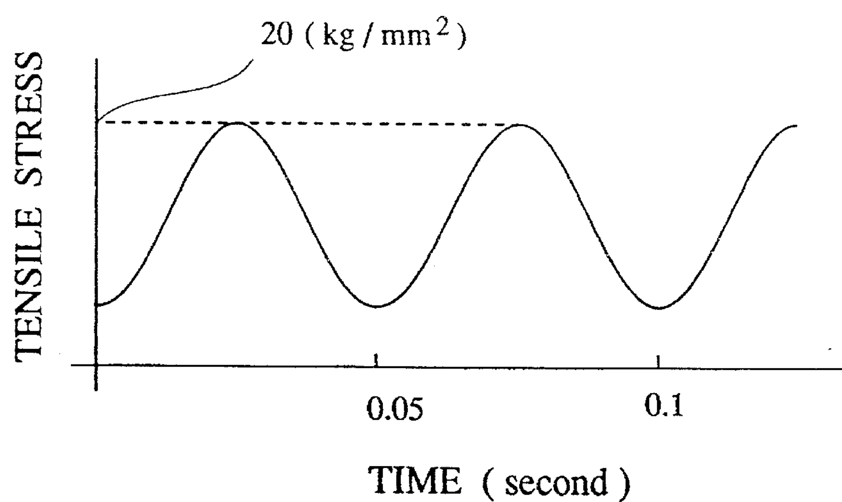
FIG. 5 is a graph showing the amplitude of the tensile stress applied to the FRP test piece in Example 1, which was changeable with time.

As is shown in FIG. 4, both ends of the FRP test piece 13 were gripped by jigs 14, 14 in a tensile machine (5-ton hydraulic fatigue test machine, manufactured by Sam Denshi Kikai K. K.). A sensing coil 15 was disposed around the FRP test piece 13 along the entire length of the FRP test piece 13. A tensile stress having an amplitude changeable in a sinusoidal manner as shown in FIG. 5 (20 Hz and 2–20 $kg/mm^2$) was applied to the FRP test piece 13 in the directions shown by the arrows D, D' in FIG. 4 in order to conduct the fatigue test. With a magnetic sensor comprising a sensing coil 15 and an impedance analizer 16, the inductance was detected under the conditions described as follows:

Sensing coil 15: Surrounding-type (number of turns: 200).

Fundamental inductance: 10 mH.

The measurement of the inductance was conducted at the $10^N$-th cycle (where N=1, 2,.3, . . . ). The FRP test piece 13 was broken at the level of the $10^7$-th stress cycle. The results are shown in FIG. 6.

As is clear from FIG. 6, the inductance was substantially constant in an earlier stage of the fatigue test, but it increased drastically just before the fracture of the FRP test piece took place.

EXAMPLE 2

Amorphous wires having a composition consisting essentially of 66.5 atomic % of Fe, 8.5 atomic % of Si, 12 atomic % of B, 11 atomic % of Co, and 2 atomic % of Cr and having an average diameter of 125 μm were placed at a pitch of 0.3 mm between plies of cloths constituted by carbon fibers having an average diameter of 6 μm and an epoxy resin in the step of laying-up 40 plies of the carbon fiber cloths. The resulting laminate was heat-cured at 180° C. for two hours to produce an FRP member test piece. In the FRP test piece, a v/f of the carbon fibers was 57%, a v/f of the amorphous wires was 3%, and a v/f of the epoxy resin was 40%.

Figure 7:
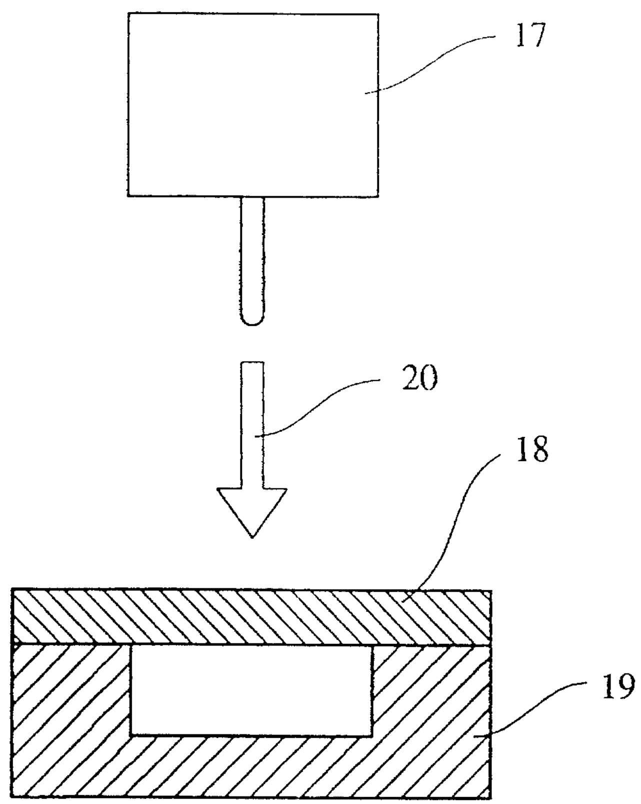
FIG. 7 is a schematic view showing a way of applying an impact energy to the FRP test piece in Example 2.
Figure 8:
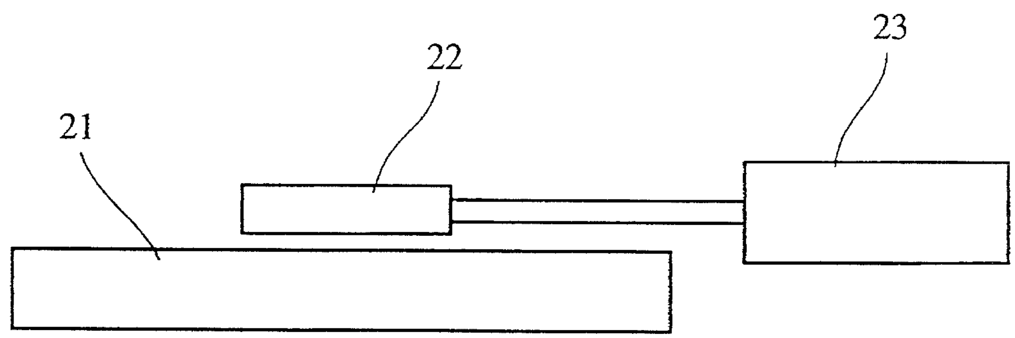
FIG. 8 is a schematic view showing the method of detecting the magnetic properties of the magnetic members in the FRP test piece in Example 2.

As is shown in FIG. 7, the FRP test piece 18 was set on a base plate 19 with a recess in an impact test machine, and a weight 17 was dropped onto the FRP test piece 18 to add various levels of impact energy thereto. The impact absorption energy given to each FRP test piece 18 was between 0 and 9 Joules. With a magnetic sensor comprising a sensing coil 22 and a detector (distortion factor-detecting means) 23 as shown in FIG. 8, the distortion factor of the FRP test piece was measured under the following conditions:

Sensing coil 22: Pick-up type.

Number of turns: Primary coil: 200 (70 turns/mm), and Secondary coil: 200.

Initial distortion factor: 2.1%.

Figure 9:
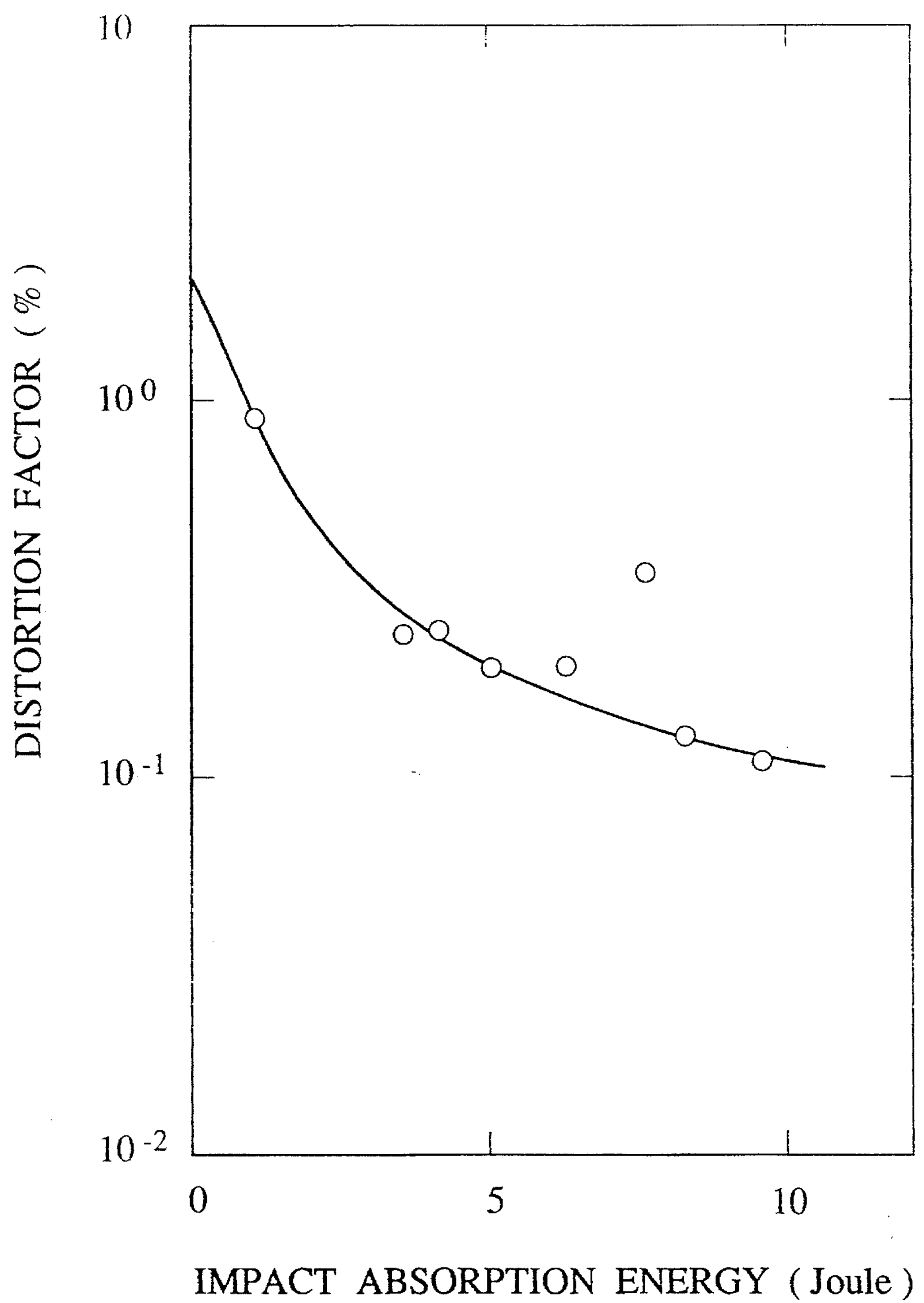
FIG. 9 is a graph showing the relation between the impact absorption energy applied to the FRP test piece and the distortion factor detected by a magnetic sensor.

The results are shown in FIG. 9. Incidentally, the FRP test piece 21 had no visible damage after the impact test.

As is clear frown FIG. 9, the distortion factor of the FRP member decreased with the increase in the impact absorption energy of the FRP test piece 21. From this relation, it can be determined by measuring the distortion factor without coming into contact with the FRP member (by a non-destructive inspection method) whether or not the FRP member has suffered from a fatal impact damage, for instance, with a standard that the impact absorption energy of 5 Joule or more causes a fatal internal damage in the FRP member.

As described above in detail, by detecting the change in the magnetic properties of the magnetic members contained in the FRP member with a magnetic sensor, the internal damage of the FRP member can easily be detected by a non-destructive method. Accordingly, the quality of the FRP members is not degraded even after the test is repeated. Further, the method of the present invention is applicable to any FRP members having complicated shapes.

What is claimed is:

1. A method of detecting an internal damage in a fiber-reinforced plastic member which has been subjected to stress, said fiber-reinforced plastic member being composed of reinforcing fibers, a matrix resin, and magnetic members in a form of fibers or ribbons having a magneto-mechanical property and subjected to an initial internal stress, comprising the steps of:

(a) applying a magnetic field to said magnetic members in said fiber-reinforced plastic member;

(b) measuring a magnetic property of said magnetic members;

(c) comparing a measured value of the magnetic property of said magnetic members with an initial value of the magnetic property of said magnetic members to ascertain any difference between the measured and initial values; said initial value being measured on said magnetic members placed under said initial internal stress only; and (d) determining, based on the result of said comparing step (c), whether or not any internal damage is created due to a release of the initial internal stress on said magnetic members caused by said internal damage.

2. The method of detecting an internal damage in a fiber-reinforced plastic member according to claim 1, wherein said magnetic members are amorphous wires.

3. The method of detecting an internal damage in a fiber-reinforced plastic member according to claim 1, wherein said internal damage is microcracks.

4. A method of detecting an internal damage in a fiber-reinforced plastic member which has been subjected to stress, said fiber-reinforced plastic member being composed of reinforcing fibers, a matrix resin, and magnetic members having a magneto-mechanical property and subjected to an initial internal stress, said magnetic members being in a form of fibers or ribbons and combined with said reinforcing fibers to form blended yarns, which are disposed on cloths of said reinforcing fibers and then impregnated with said matrix resin to produce said fiber-reinforced plastic member, comprising the steps of:

(a) applying a magnetic field to said magnetic members in said fiber-reinforced plastic member;

(b) measuring a magnetic property of said magnetic members;

(c) comparing a measured value of the magnetic property of said magnetic members with an initial value of the magnetic property of said magnetic members to ascertain any difference between the measured and initial values; said initial value being measured on said magnetic members placed under said initial internal stress only; and (d) determining, based on the result of said comparing step (c), whether or not any internal damage is created, due to a release of the initial internal stress on said magnetic members caused by said internal damage.

5. The method of detecting an internal damage in a fiber-reinforced plastic member according to claim 4, wherein said blended yarns are woven with said reinforcing fibers to form blended yarn fabrics, which are disposed on cloths of said reinforcing fibers and then impregnated with said matrix resin to produce said fiber-reinforced plastic member.

6. The method of detecting an internal damage in a fiber-reinforced plastic member according to claim 4, wherein said magnetic members are amorphous wires.

7. The method of detecting an internal damage in a fiber-reinforced plastic member according to claim 4, wherein said internal damage is microcracks.

* * * * *